United States Patent [19]

Raina et al.

[11] Patent Number: 6,087,165

[45] Date of Patent: Jul. 11, 2000

[54] RECOMBINANT BACULOVIRUS AND ITS USE AS A BIOCONTROL AGENT FOR CROP PESTS

[75] Inventors: Ashok K. Raina, New Orleans, La.; Robert F. Leclerc, Waterford, Mich.; Vikram N. Vakharia, Bowie, Md.

[73] Assignee: The United States of America as represented by the Secretary of Agriculture, Washington, D.C.

[21] Appl. No.: 09/258,275

[22] Filed: Feb. 26, 1999

[51] Int. Cl.[7] .................................................. C12N 15/00
[52] U.S. Cl. .................. 435/320.1; 536/23.4; 536/23.5; 536/23.51
[58] Field of Search .................................. 435/69.1, 69.4, 435/69.8, 235.1, 320.1; 536/23.4, 23.5, 23.51

[56] References Cited

PUBLICATIONS

Luckow, Current Opinions in Biotechnology, vol. 4(5), pp. 1–15, Jul. 1993.

Vakharia et al., *Insect Biochem. Molec. Biol.,* vol. 25(5), pp. 583–589, 1995.

Blackburn et al., *J. Insect Physiol.,* vol. 41(8), pp. 723–730, 1995.

H. Alan Wood, *Molecular Biology of the Biological Control of Pests and Diseases of Plants,* pp. 91–104, 1996.

*Altered Baculovirus Dooms Corn Earworms,* Agricultural Research, Mar. 1998.

*Primary Examiner*—David Guzo
*Attorney, Agent, or Firm*—M. Howard Silverstein; John D. Fabo; Janelle S. Graeter

[57] ABSTRACT

Recombinant baculoviruses were prepared which contain sequences expressing peptide hormones which cause lack of feeding in *Helicoverpa zea* (corn earworm) and related pestw. The peptides were isolated from *H. zea* and identified as helicokinins. When present in sufficient amounts in the insect, weight and water loss and the eventual death of the insect occurs.

10 Claims, 3 Drawing Sheets

GTGCGCTTCTCACCTTGGGGC<u>GGCTAA</u>

FIG. 2a

```
GATCTATGGTGGGTCCTTGCATGCTGCTCTTGCTGTGCTCCTGG
    |——————————————signal sequence——————————
GCCTGAGACTCCAGCTCTCCCTCGGTGTGCGCTTCTCACCTTGG
——————————————————>|—————HK-II—————
GGCGGCTAAGGATCC
—————>*BamHI
```

FIG.2b

RECOMBINANT BACULOVIRUS AND ITS USE AS A BIOCONTROL AGENT FOR CROP PESTS

BACKGROUND OF THE INVENTION

1. Field of the Invention

Scientists are currently seeking effective alternatives to conventional chemical methods for crop pest management. One promising approach has been the application of biological control agents. The discovery and development of biological systems which are detrimental to targeted pests but harmless to the environment have thus assumed a high priority. This invention relates to baculoviruses genetically engineered to produce a peptide hormone which, when present in sufficient amounts, results in weight and water loss and the eventual death of these insects. Such peptides have been isolated from the corn earworm *Helicoverpa zea* and related species, and have been identified as helicokinins.

2. Description of the Relevant Art

Insect infestation is a major cause of crop loss throughout the United States. The corn earworm *Helicoverpa zea* (*H. zea*) causes an estimated $1.2 billion in crop damage each year and, together with *Helicoverpa armigera* (*H. armigera*) and a related species, *Heliothis virescens* (*H. virescens*), constitutes the most important group of crop pests throughout the world. *H. zea* and *H. armigera* together cause crop damage resulting in losses worth over $5 billion annually.

Chemical pesticides have conventionally been relied upon to control insect pest populations. Environmental and consumer safety concerns, however, have led to the deregistration of many pesticides and a reluctance to use others on agricultural products which are ultimately intended for human or animal consumption. In addition, the increasing resistance of insects to chemical pesticides has resulted in a reduction in their susceptibility to the insecticidal activity of the chemicals. Scientists have therefore pursued the development of biological agents as an alternative for effective control.

Attempts have been made to exploit the natural sex attractants of insects in order to disrupt reproductive behavior. Sekul et al. [*J. Econ. Entomology.* 1975. vol. 68(5), pp. 603–604], for example, identified a compound, Z-11-hexadecenal, which is produced and released by the adult female of *H. zea* and referred to as a sex attractant inhibitor. Sparks et al. (*Southern Cooperative Series Bulletin.* 1988. pp. 50–65) discussed Heliothis pheromones and their potential use as biocontrol agents by mating disruption. Raina et al. (U.S. Pat. No. 5,032,567, 1991) disclosed a neuropeptide referred to as Hez-PBAN. The peptide was isolated from *H. zea* adults and activated pheromone biosynthesis in female moths as well as melanization in the larvae. Pheromone production at the wrong time of day can prove hazardous to females, and larval melanization is often fatal. Kingan et al. (U.S. Pat. No. 5,344,821, 1994) disclosed a pheromonostatic polypeptide obtained from male *H. zea* which, upon injection into the female, stops pheromone production and renders the female unattractive to male insects.

Another approach involved the use of baculoviruses (Wood, H. A. 1996. In *Molecular Biology of the Biological Control of Pests and Diseases of Plants.* Gunasekaran and Weber, ed., CRC Press, Inc., Boca Raton, Fla., pp. 91–104, herein incorporated by reference). Naturally-occurring baculoviruses are known insect pathogens capable of effecting reduction in insect populations. This capability led to the expectation that the viruses could be utilized safely and effectively in biological control applications. In addition, recombinant baculoviruses expressing various pesticidal genes have been produced.

While these approaches have shown potential for controlling corn earworm populations, consistent success has proven elusive and difficult to achieve for various reasons: lack of an effective carrier or vector in the case of mating disruption, the high cost of production and low activity in the case of naturally-occurring baculoviruses and the lack of culture systems necessary for propagating recombinant baculoviruses. The need for a reliable and consistent means for controlling *H. zea* populations in the field thus remains an important goal.

SUMMARY OF THE INVENTION

Recombinant techniques have provided the opportunity for improving the capability of the baculovirus system for insect control. Foreign genes inserted into the baculovirus genome are expressed after virus infection, thus providing targeted delivery of insect-controlling substances to particular insect hosts.

We have discovered that DNA encoding a peptide having helicokinin activity may be incorporated into a baculovirus for expression. The baculovirus then serves as a vector for transmission of the peptide to insects which feed upon and ingest the recombinant baculovirus. Expression of the peptide then occurs in the insect and results in insect death.

In accordance with this discovery, it is an object of the invention to provide a novel recombinant baculovirus useful for controlling populations of *Helicoverpa* and related species by expressing a peptide having helicokinin activity.

Other objects and advantages will become readily apparent from the following description.

BRIEF DESCRIPTION OF THE DRAWINGS

FIG. 2, A) shows the sequence of the synthesized DNA encoding the peptide having HK-II activity with the codon for glycine at the 3' end for glycine-directed amidation and a termination codon (SEQ ID NO: 1). B) shows the sequence of the oligonucleotide encoding the human placental alkaline phosphatase signal sequence and the peptide having HK-II activity with GATC extensions for BamHI and BglII cloning sites (SEQ ID NO: 2).

DETAILED DESCRIPTION OF THE INVENTION

Figure 1:
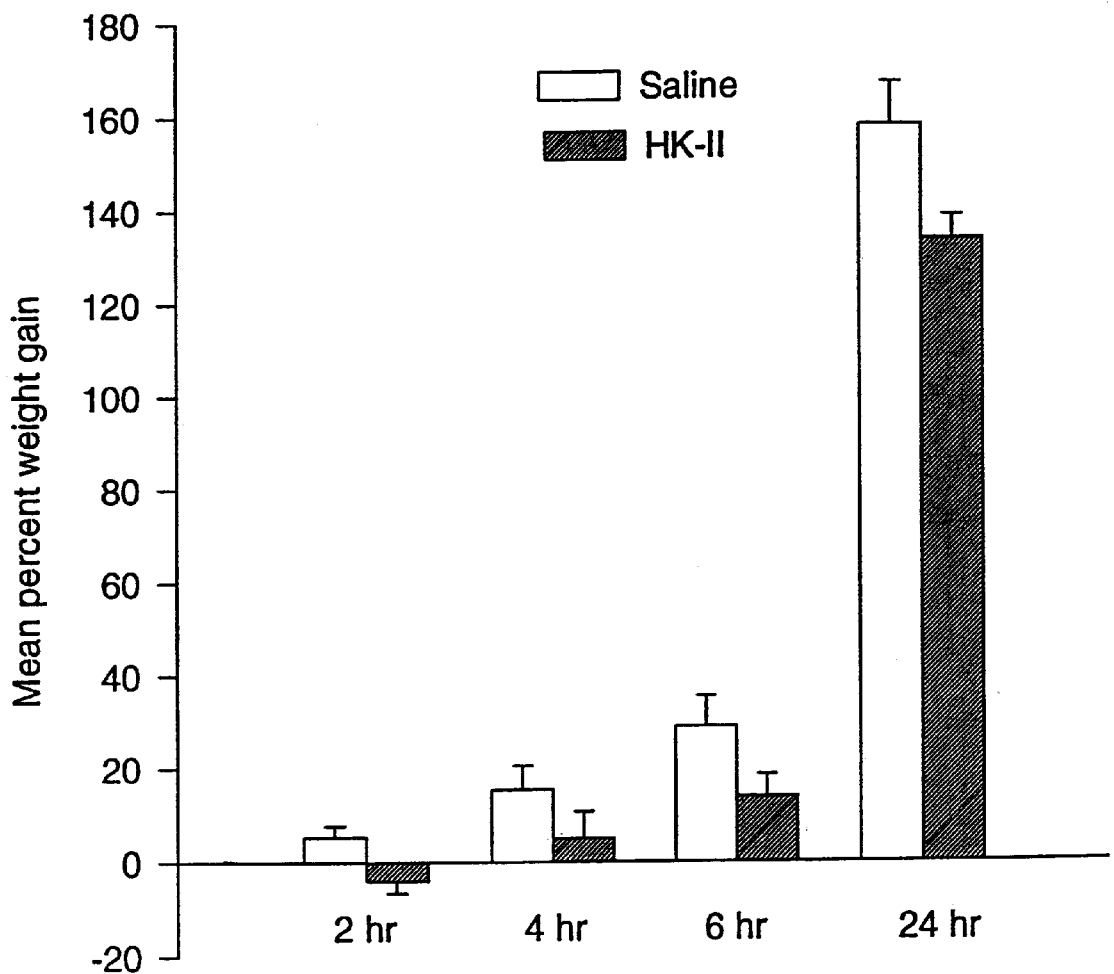
FIG. 1 shows effects of the peptide hormone helicokinin-II (HK-II) when injected into newly moulted $5^{th}$ instar *H. zea* larvae.

*Helicoverpa zea* and *H. armigera*, together with related species *Heliothis virescens,* constitute an important group of crop pests, causing billions of dollars in damage throughout the world. Due to problems associated with the use of chemical pesticides, there has been a continuing emphasis on the development of biological control compositions and methods. As mentioned previously, baculoviruses are known insect pathogens and, as such, have presented an opportunity for use as biocontrol agents (Wood, supra). Moreover, new methods for the propagation of the viruses have resulted in a renewed interest in their use. Baculoviruses kill their hosts very slowly, however, after most of the feeding damage has already occurred. Improvements were therefore required in order for baculovirus systems to effectively serve as biocontrol agents.

A number of peptides were isolated from the nervous system of *H. zea* and the tobacco hornworm, *Manduca sexta* (Blackburn et al. 1995. *J. Insect Physiol.* vol. 41, no. 8, pp. 723–730, herein incorporated by reference) and screened for the ability to cause feeding inhibition and growth retardation in *H. zea* larvae (see Table 1). Three helicokinin peptide hormones were designated helicokinin-I (HK-I), helicokinin-II (HK-II) and helicokinin-III (HK-III) and have the amino acid sequences YFSPWG SEQ ID NO: 3, VRF- SPWG SEQ ID NO: 4 and KVKFSAWG (SEQ ID NO: 5), respectively. These peptides help regulate the physiological processes enabling the insect to grow from caterpillar to adult moth. When injected into newly moulted $5^{th}$ instar *H. zea* larvae, they were found to cause significant weight loss. The weight loss was associated with lack of feeding and excessive water loss; however, in studies utilizing HK-II, the effect only lasted for up to 6 hours (FIG. 1), probably due to breakdown of the injected peptide. In order to prolong the effect for a time sufficient to result in the death of the insect, continuous injections would be required. A practical approach for administration of peptide was thus necessary in order for it to be useful on a scale which would result in effective biocontrol.

TABLE 1

Screening of Peptides for Feeding Inhibition and Growth Retardation in *Helicoverpa zea* Larvae.

| Test | Amino Acid | | % Weight Gain in | | Dry weight of |
|---|---|---|---|---|---|
| Material* | Residues | N | 6 Hrs | 24 Hrs | Feces (mg) |
| Saline | — | 20 | 33.7 | 128.3 | 36.0 |
| Mas-MIP-I | 9 | 10 | — | 120.2 | 38.1 |
| Mas-MIP-II | 9 | 10 | 31.2 | 117.5 | 32.6 |
| Mas-MIP-III | 12 | 10 | 37.8 | 103.1 | 33.1 |
| Mas-MIP-IV | 9 | 9 | 33.1 | 110.0 | 33.4 |
| Mas-MIP-V | 9 | 10 | 29.6 | 122.0 | 34.0 |
| Mas-MIP-VI | 9 | 10 | 31.1 | 121.6 | 33.8 |
| Hez-K-I (HK-I) | 6 | 10 | 22.4 | 117.4 | 34.0 |
| Hez-K-II (HK-II) | 7 | 10 | 19.2 | 95.9 | 33.9 |
| Hez-K-III (HK-III) | 8 | 10 | 20.7 | 95.8 | 33.9 |
| FLRFa-10 | 10 | 10 | 24.2 | 115.1 | 42.2 |
| FLRFa-24 | 24 | 10 | 24.4 | 120.4 | 40.5 |
| FLRFa-39 | 39 | 10 | 22.8 | 86.1 | 25.4 |

*100 pmol of each peptide was dissolved in 5 μl of *Heliothis virescens* saline and injected into a newly moulted $5^{th}$ instar larva after $CO_2$ anasthesia. After ten min recovery on ice, the larvae were placed on a known amount of diet in a Petri dish and kept in constant darkness at 23° C.; N=sample size.

While any one of the peptides having the helicokinin properties may be utilized, HK-II and HK-III are of particular interest. By way of example, a recombinant baculovirus containing DNA encoding the HK-II peptide was prepared and tested for its ability to express the peptide in sufficient quantities in the insect to result in insect death.

The recombinant baculovirus was prepared using conventional recombinant techniques. A synthetic oligonucleotide encoding the peptide was commercially prepared from codon preferences based on 39 structural genes from *M. sexta, H. zea* and Heliothis spp. (FIG. 2A) SEQ ID NO: 1.

A GGC codon encoding glycine was incorporated at the 3' end of the HK-II coding region to effect amidation, thus ensuring biological activity, followed by a TAA stop codon. In addition, oligonucleotides for a signal sequence were inserted at the 5' end of the coding sequence. The protein expressed by the sequence provides a degree of protection for the small peptides. Such sequences are well-known to those of skill in the art and may be selected according to the particular desireable functions. For example, the human placental alkaline phosphatase signal sequence (Mroczkowski et al. 1994. *J. Biol. Chem.* vol. 269, no. 18, pp. 13522–13528, herein incorporated by reference) has been shown to be effective at directing export of polypeptides in insects, thus providing the added benefit of targeting the peptide to areas of optimal efficacy.

A vector was prepared by cloning the synthetic oligonucleotide into a plasmid capable of transfecting baculoviruses. Plasmids effective for this purpose are commercially available and include but are not limited to pAcUW42, pAcUW43 (PharMingen, San Diego, Calif.) and pAcUW31 (Clone Tech Labs, Inc., Palo Alto, Calif.). The oligonucleotide may be modified to include sequences required for insertion into the plasmid. For purposes of example, the plasmid pAcUW42 was utilized as a baculovirus transfer vector with modifications as described in Example 1 and shown in FIG. 2B (SEQ ID NO: 2). In a preferred embodiment, in order to express larger quantities of the peptide, two copies of the HK-II DNA were cloned into the transfer vector, as described in Example 2. The vectors were designated pHK-$II_1$, containing a single copy, and pHK-$II_2$, containing two copies.

Transfection of the baculovirus was carried out as described in Example 3. Appropriate insect cell cultures were established, followed by co-transfection with pHK-$II_1$ or pHK-$II_2$ and linearized baculovirus DNA in transfection buffer. The HK-II DNA was integrated into the baculovirus DNA by homologous recombination. Appropriate insect cells include *Spodoptera frugiperda* Sf-9 and Sf-21 cells. Preferred are Sf-9 cells. Linearized baculovirus DNA may be obtained from nuclear polyhedrosis viruses *Autographa californica* (ACMNPV, PharMingen, supra) or *Bombyx mori* (BmNPV).

Viable baculovirus progeny were collected from the cell culture medium and recombinants selected by an effective selection means. For example, viral dilutions may be used for plaque formation, and recombinants differentiated from wild-type by color selection using chromogenic substrates, such as X-Gal (PharMingen, supra) incorporated in an agarose overlay. After selection, recombinant baculovirus is plaque purified and propagated in appropriate insect cells, such as Sf-9 or Sf-21.

Recombinant viruses, designated vHK-$II_1$ and vHK-$II_2$, were tested for efficacy against *H. zea* larvae, as described in Example 4. Larvae were fed on both vHK-$II_1$ and vHK-$II_2$ as well as control (Sf-9 cells) and wild-type baculovirus. Results are shown in Table 2. The control larvae were in the $4^{th}$ instar and weighed an average of 119 mg, the larvae fed on vHK-$II_2$ weighed only 18.8 mg and all were in $2^{nd}$ instar. After 20 days, all the larvae had pupated in the control group and 50% in the wild-type group; 3.3% of the larvae in the vHK-$II_2$ group had pupated, and 93.3% were dead. The virus containing HK-$II_2$ was more effective than that containing HK-$II_1$. In a field situation, with less than optimal environmental conditions and no feeding, insect mortality is expected to be even more severe.

TABLE 2

Effect of Recombinant Baculovirus on Growth and Mortality in *Helicoverpa zea* Larvae.

| Treat- | After 8 Days | | After 20 Days | |
|---|---|---|---|---|
| ment | Ave. Wt. (mg) | Ave. Instar | % Pupated | % Mortality |
| Control (Sf-9 Cells) | 119.0 ± 7.6 | 3.8 | 100.0 | 0.0 |
| Wild Type (AcMNPV) | 86.8 ± 13.8 | 3.3 | 50.0 | 30.0 |
| VHK-$II_1$ (single copy) | 44.6 ± 9.6 | 2.7 | 17.2 | 75.9 |
| VHK-$II_2$ (two copies) | 18.8 ± 5.7 | 2.9 | 3.3 | 93.3 |

Newly-hatched larvae were placed on artificial diet smeared with control, wild-type or the recombinant viruses in petri dishes. Larvae were allowed to feed for 48 hours, in continuous darkness. After 48 hours, 30 larvae from each petri dish were transferred singly to 30-ml diet cups. Values in the first column are averages ± SEM (N=30).

The following examples are intended only to further illustrate the invention and are not intended to limit the scope of the invention as defined by the claims.

EXAMPLES

Example 1

Synthesis of DNA encoding HK-II.

Synthetic DNA encoding the seven-amino acid HK-II peptide for insertion into the baculovirus genome was commercially prepared on the basis of codon preferences based on 39 structural genes from *M. sexta, H. zea* and Heliothis spp. A GGC codon to allow for glycine-directed amidation was incorporated at the 3' end of the HK-II coding region, followed by a TAA stop codon. A signal sequence of human placental alkaline phosphatase DNA (Stratagene, La Jolla, Calif.) was fused to the 5' end of the HK-II coding region (Mroczkowski et al., supra). This sequence has been shown to be effective at directing export of polypeptides in insects. A GATC extension was added at the 5' end of the signal sequence in order to permit cloning into BamHI and BglII cloning sites of the baculovirus transfer vector.

Example 2

Cloning HK-II DNA into baculovirus transfer vector.

The construct described in Example 1 was cloned into the baculovirus transfer vector pAcUW42 (PharMingen, supra) using conventional cloning procedures (Sambrook et al., 1989. *Molecular Cloning: A Laboratory Manual*. Cold Spring Harbor Laboratory, Cold Spring Harbor, N.Y., herein incorporated by reference). The GATC extension created a Sau3A site for cloning into BamHI and BglII sites. Oligonucleotides encoding signal peptide and HK-II were annealed and cloned downstream of both strong late p10 and polyhedrin promoters, thus producing a vector having two copies of the HK-II DNA.

Twenty-five pmol phosphorylated oligonucleotides were annealed at 65° C. for 30 min, with cooling to ambient temperature to yield double stranded signal and HK-II sequences. Full length constructs were agarose gel-purified using the MERmaid Kit protocol (Bio 101, Vista, Calif.), ligated to BamHI-digested and dephosphorylated pAcUW42 baculovirus transfer vector DNA and used to transform competant *E. coli*-derived DH5α cells. Insert orientation was determined by restriction endonuclease digestion, and the nucleotide sequence verified by dideoxy chain termination sequencing method using T7 Gene 6 kit (US Biochemical, Cleveland, Ohio) and a polyhedrin promoter primer (5'AAATGATAACCATCTCGC3' SEQ ID NO: 6). The construct was designated HK-II$_1$.

To produce the two-copy construct, HK-II$_1$ was cleaved upstream of the signal sequence ATG codon and downstream of the TAA termination codon using Sau3A restriction enzyme. The fragment was gel-purified and subcloned into BglII-digested and dephosphorylated HK-II$_1$ construct to yield HK-II$_2$ plasmid containing two copies of the HK-II gene.

Example 3

Transfection of baculovirus.

*Spodoptera frugiperda*, Sf-9, and *Trichoplusia ni*, Tn 'High Five' cells were cultured as monolayers in 75 cm$^2$ tissue culture flasks at 27±0.5° C. either in TMN-FH insect media (Life Technologies, Gaithersburg, Md.) supplemented with 10% fetal calf serum and antibiotic+fungicide for Sf-9 cells, or in EX-CELL 400 (JRH Biosciences, Lenexa, Kans.) insect media for 'High Five' cells. Sf-9 cells were co-transfected with 5 µg of HK-II$_1$ or HK-II$_2$ plasmid DNA and 0.5 µg linearized AcUW1.lacZ DNA in transfection buffer (PharMingen, supra). HK-II DNA was integrated into linearized AcUW1.lacZ baculovirus DNA (PharMingen, supra) via homologous recombination. Supernatant containing viable viral progeny resulting from the homologous recombination between the transfer vector and AcUW1.lacZ was collected after 6 days. Viral dilutions were used for plaque assays. Recombinants were differentiated from wild-type by color selection by incorporation 250 µg/ml X-Gal in the agarose overlay. The recombinant baculovirus was plaque purified and propagated in Sf-9 cells.

Example 4

Effects of recombinant baculovirus on *H. zea* larvae.

Newly hatched *H. zea* larvae were placed on a diet containing Sf-9 cells (control), wild-type baculovirus AcM-NPV (negative control), vHK-II$_1$ or vHK-II$_2$ and allowed to feed for 48 hours. The larvae were then transferred singly to 30-ml diet cups. After 8 days, the larvae in all four groups were weighed and checked for instar. Results are shown in Table 2.

---

We claim:

1. A recombinant baculovirus comprising DNA encoding at least one peptide hormone having helicokinin activity.

2. The baculovirus of claim 1, wherein two copies of said DNA are present in the baculovirus.

3. The baculovirus of claim 1, wherein said DNA encodes helicokinin-II or helicokinin-III.

4. The baculovirus of claim 1, wherein said DNA encodes helicokinin-II.

5. The baculovirus of claim 1, wherein said baculovirus contains a DNA comprising a signal sequence fused to the 5' end of a sequence encoding the peptide hormone having helicokinin acitivity.

6. The baculovirus of claim 1, wherein said baculovirus is a nuclear polyhedrosis virus.

7. The baculovirus of claim 5, wherein said signal sequence is human placental alkaline phosphatase signal sequence DNA.

8. The baculovirus of claim 5, wherein said peptide hormone is helicokinin-II or helicokinin-III.

9. The baculovirus of claim 5, wherein said signal sequence is human placental alkaline phosphatase signal sequence DNA and said peptide is helicokinin-II or helicokinin-III.

10. The baculovirus of claim 6, wherein said nuclear polyhedrosis virus is *Autographa californica* nuclear polyhedrosis virus.

* * * * *

SEQUENCE LISTING

<160> NUMBER OF SEQ ID NOS: 6

<210> SEQ ID NO 1
<211> LENGTH: 27
<212> TYPE: DNA
<213> ORGANISM: Helicoverpa zea

<400> SEQUENCE: 1
gtgcgcttct caccttgggg cggctaa            27

<210> SEQ ID NO 2
<211> LENGTH: 103
<212> TYPE: DNA
<213> ORGANISM: Helicoverpa zea

<400> SEQUENCE: 2
gatctatggt gggtccttgc atgctgctct tgctgtgctc ctgggcctga gactccagct      60
ctccctcggt gtgcgcttct caccttgggg cggctaagga tcc                       103

-continued

```
<210> SEQ ID NO 3
<211> LENGTH: 6
<212> TYPE: PRT
<213> ORGANISM: Helicoverpa zea

<400> SEQUENCE: 3

Tyr Ser Phe Pro Trp Gly
  1               5

<210> SEQ ID NO 4
<211> LENGTH: 7
<212> TYPE: PRT
<213> ORGANISM: Helicoverpa zea

<400> SEQUENCE: 4

Val Arg Phe Ser Pro Trp Gly
  1               5

<210> SEQ ID NO 5
<211> LENGTH: 8
<212> TYPE: PRT
<213> ORGANISM: Helicoverpa zea

<400> SEQUENCE: 5

Lys Val Lys Phe Ser Ala Trp Gly
  1               5

<210> SEQ ID NO 6
<211> LENGTH: 18
<212> TYPE: DNA
<213> ORGANISM: Unknown
<220> FEATURE:
<223> OTHER INFORMATION: Description of Unknown Organism:Polyhedrin
      Promoter Primer

<400> SEQUENCE: 6
aaatgataac catctcgc                                                   18
```